US011781088B2

(12) United States Patent
Eychenne et al.

(10) Patent No.: US 11,781,088 B2
(45) Date of Patent: Oct. 10, 2023

(54) PROCESS FOR THE PRODUCTION AND PURIFICATION OF STEROLS

(71) Applicants: BASF SE, Ludwigshafen am Rhein (DE); BASF HEALTH AND CARE PRODUCTS FRANCE S.A.S., Levallois-Perret (FR)

(72) Inventors: Valerie Eychenne, Boussens (FR); Yannick Basso, Boussens (FR); Olivier Vallejo, Boussens (FR); Joerg Schwarzer, Monheim (DE)

(73) Assignees: BASF SE, Ludwigshafen am Rhein (DE); BASF HEALTH AND CARE PRODUCTS FRANCE S.A.S., Levallois-Perret (FR)

( * ) Notice: Subject to any disclaimer, the term of this patent is extended or adjusted under 35 U.S.C. 154(b) by 0 days.

(21) Appl. No.: 17/762,397

(22) PCT Filed: Sep. 24, 2020

(86) PCT No.: PCT/EP2020/076719
§ 371 (c)(1),
(2) Date: Mar. 22, 2022

(87) PCT Pub. No.: WO2021/058646
PCT Pub. Date: Apr. 1, 2021

(65) Prior Publication Data
US 2022/0340838 A1    Oct. 27, 2022

(30) Foreign Application Priority Data
Sep. 27, 2019 (EP) .................................... 19200121

(51) Int. Cl.
| C11C 1/10 | (2006.01) |
| B01D 9/00 | (2006.01) |
| C11B 13/00 | (2006.01) |
| C11C 3/04 | (2006.01) |
| C07J 9/00 | (2006.01) |

(52) U.S. Cl.
CPC ................ *C11C 1/10* (2013.01); *B01D 9/00* (2013.01); *C11B 13/00* (2013.01); *C11C 3/04* (2013.01); *B01D 9/0013* (2013.01); *C07J 9/00* (2013.01)

(58) Field of Classification Search
CPC ..... C11C 1/10; C11C 3/04; C11C 3/10; C11B 13/00; C07C 67/02; B01D 9/00; B01D 9/0013
See application file for complete search history.

(56) References Cited

U.S. PATENT DOCUMENTS

| 4,148,810 A * | 4/1979 | Struve ........................ C07J 9/00 |
| | | 552/545 |
| 5,627,289 A | 5/1997 | Jeromin et al. |
| 2002/0058827 A1* | 5/2002 | Wollmann ................. C07J 9/00 |
| | | 552/544 |
| 2002/0082434 A1* | 6/2002 | Bonakdar .................. C07J 9/00 |
| | | 552/545 |
| 2004/0260104 A1 | 12/2004 | Sicre et al. |
| 2013/0274489 A1 | 10/2013 | Lemp et al. |

FOREIGN PATENT DOCUMENTS

| EP | 0333472 A2 | 9/1989 |
| EP | 0610742 A1 | 8/1994 |
| EP | 0656894 B1 | 2/1998 |
| EP | 1179535 A1 | 2/2002 |
| EP | 1179536 A2 | 2/2002 |
| EP | 1169335 B1 | 11/2003 |
| EP | 2635592 B1 | 8/2017 |
| GB | 2145079 A | 3/1985 |
| WO | 2004/000979 A1 | 12/2003 |
| WO | 2005/051294 A2 | 6/2005 |

OTHER PUBLICATIONS

International Search Report and Written Opinion received for PCT Patent Application No. PCT/EP2020/076719, dated Dec. 21, 2020, 7 pages.

* cited by examiner

*Primary Examiner* — Yate' K Cutliff

(74) *Attorney, Agent, or Firm* — Faegre Drinker Biddle & Reath LLP

(57) ABSTRACT

The presently claimed invention relates to a process for the production and purification of sterols from oil distillates or oil distillation residues, in particular from the latter. Specifically, the presently claimed invention relates to a process for obtaining sterols in a pure form with reduced impurity and improved color.

21 Claims, No Drawings

PROCESS FOR THE PRODUCTION AND PURIFICATION OF STEROLS

CROSS-REFERENCE TO RELATED APPLICATIONS

This application is a national stage application (under 35 U.S.C. § 371) of PCT/EP2020/076719, filed Sep. 24, 2020, which claims benefit of European Application No. 19200121.2, filed Sep. 27, 2019, both of which are incorporated herein by reference in their entirety.

FIELD OF THE INVENTION

The presently claimed invention relates to a process for the production and purification of sterols from oil distillates or oil distillation residues, in particular from the latter. Specifically, the presently claimed invention relates to a process for obtaining sterols in a pure form with reduced impurity and improved color.

BACKGROUND OF THE INVENTION

The production of sterols from distillates obtained in the deacidification of vegetable oils or from distillation residues accumulating in the production of methyl esters and more particularly in the production of methyl esters from crops for "biodiesel" applications is generally known.

Phytosterols and their esters possess hypocholesterolaemic properties, i.e. these substances are capable of lowering the cholesterol level in the blood. Accordingly, they are used as food additives, for example for the production of margarine, frying oils, sausages, ice creams and the like. The production of sterols and other unsaponifiable constituents, such as tocopherols for example, from distillates obtained in the deacidification of vegetable oils has already been variously described in the patent literature, cf. EP-A2 0 610 742 (Hoffmann-LaRoche), GB-A1 2,145,079 (Nisshin Oil Mills Japan) and EP-A1 0 333 472 (Palm Oil Research and Development Board).

EP 0 656 894 B1 (Henkel) describes a process for the production of sterols in which a residue from the distillation of methyl esters consisting essentially of glycerides, sterols, sterol esters and tocopherols is transesterified with methanol in the presence of alkaline catalysts. After neutralization of the catalyst, removal of the excess methanol by distillation and, optionally, removal of the catalyst by washing, the sterols are crystallized by lowering the reaction temperature from about 65 to 20° C. The thus obtained crystals are washed with methanol and water. Unfortunately, the yield of sterols is unsatisfactory.

EP 2 635 592 B1 (Verbio) discloses a method for obtaining phytosterols and tocopherols using multi-phase separation systems to isolate the sterol and/or tocopherol.

EP1179535 B1 and EP1179536 B1 (both: BASF) disclose processes for the production of sterols using a two-step-transesterification to obtain sterols from vegetable oil distillates. Crystallization of the obtained sterols and washing with methanol and fatty acid methyl ester (FME) is disclosed as subsequent process steps in dependent claims. Although in EP1179536 B1 "methyl ester" is disclosed as employed solvent in the examples, the "methyl ester" actually used in the examples and disclosed in the description is the FME from the transesterifications of the vegetable oil. EP1179535 B1 discloses in its examples the use of "FME"; in [0036] and [0042] EP1179535 B1 also discloses that the crystals obtained in examples a) and b) "are washed with suitable solvents". However, which solvents those actually might be is not disclosed.

EP1169335 B1 (BASF) discloses a process for the crystallization of sterols from a specific mixture of methanol and FME in certain ratios and washing of the obtained crystals. Objective of this disclosure is to provide sterols in high yields and "good color quality". Key is according to this disclosure the optimum amount and ratio of methanol during crystallization and thus the crystallization temperature which is said to lead to the desired improvement. The obtained crystals are then washed with FME, which step is said to further improve the color quality of the sterol crystals obtained.

It is to be noted that the "methyl ester" disclosed by EP1169335 B1 clearly is the "FME", as both descriptions/terms are used interchangeably as can be seen from e.g. [0008], which mentions twice the washing of the crystals but uses "methyl ester" at the first occasion and "FME" on the second occasion. Claim 1 in the binding German version thus correctly uses the term "FME" (whereas claim 1 in the English translation using incorrectly the term "fatty acid ester").

Accordingly, the problem addressed by the presently claimed invention is to provide sterols in high yields and high purity by an economic process that would avoid high pressure reactions and, at the same time, to utilize residues from the distillation of transesterified oils more economically.

Several methods are reported for the production of sterols from distillates. However, it is still a challenge to perform a process with improved yield of sterols without the use of toxicologically and ecologically unsafe solvents. Further, improving the color of the sterols with high purity also remains a challenge.

SUMMARY OF THE INVENTION

It has surprisingly been found that the yield, color and purity of the phytosterols is significantly influenced by the process that is used for the downstream processing of the vegetable oil distillate and the solvent used for purification. Thus, the choice of solvent used for the purification process plays a significant role in improving the color of the phytosterol and reducing the level of impurities without compromising on the yield of the final product.

Hence, the presently claimed invention generally relates to sterol production and more particularly to a process for the production of sterols from residues of the distillation of transesterified oils. In order to be able to obtain sterols in pure form, they have to be converted from the esterified to the free state, otherwise they are very difficult to separate from the components accompanying them. The conversion into free sterols may be carried out, for example, by hydrolysis, saponification or transesterification. The presently claimed invention is directed to the use of transesterification mechanisms. Moreover, the present invention relates to a purification process, wherein the color of the final phytosterol product is significantly improved and the amount of phytosterol ester as an impurity as well as the solvent content is significantly reduced.

These improvements have been achieved with the process for producing and purifying sterols according to the present invention, said process comprising at least the steps of:

(a) providing an oil distillate or, preferably, an oil distillation residue, said distillate or residue comprising sterol esters and partial glycerides;

(b) optionally transesterifying the partial glycerides with a lower alcohol in the presence of a basic catalyst to form fatty acid alkyl esters and glycerol;
(c) in case step (b) is applied, removing at least partially the excess lower alcohol, the basic catalyst, the glycerol and/or the fatty acid alkyl esters, preferably at least the lower alcohol and the fatty acid alkyl esters, more preferably at least the lower alcohol, glycerol and the fatty acid alkyl esters, and most preferably all four, each of the components either in one single step or as two, three or more steps with the individual or joint removal of the components being performed in parallel or sequentially, to form a product comprising the sterol esters;
(d) optionally subjecting the distillate or residue or—if steps (b) and (c) are applied—the product resulting from step (c) to a purification step using adsorbents;
(e) transesterifying the sterol esters in the distillate or residue or—if steps (b) and (c) are applied—the product resulting from step (c)—or if step (d) is applied—step (d) with a lower alcohol in the presence of a basic catalyst to form free sterols;
(f) optionally removing at least partially the excess lower alcohol, the basic catalyst, the glycerol and/or the fatty acid alkyl esters, preferably at least the lower alcohol and the fatty acid alkyl esters, more preferably at least the lower alcohol, glycerol and the fatty acid alkyl esters, and most preferably all four, each of the components either in one single step or as two, three or more steps with the individual or joint removal of the components being performed in parallel or sequentially;
(g) optionally adding water to the product resulting from step (e) or—if step (f) is applied—step (f), the water being added in an amount ranging from 15% to 25% based on the mass of a total batch in order to set a mass ratio of sterol:fatty acid alkyl ester (calculated as FME):lower alcohol (calculated as methanol):water of substantially 1:2.5-3:2.2-2.5:0.8-1.2, during the addition of water homogenizing the reaction mixture to form an emulsion/suspension by mixing;
(h) crystallizing sterols in the mixture obtained from step (e), (f) or (g)—depending if such steps are employed or not—, optionally under mixing;
(i) removing of the sterol crystals by physical means from the mother liquor;
(j) washing the sterol crystals obtained in step (i) in a separate or combined washing with solvent, wherein the solvent is an organic solvent and/or a solvent mixture of more than one organic solvents optionally but not preferred also containing water, preferably a solvent mixture that comprises at least one aprotic polar solvent, more preferably a solvent mixture of at least one protic polar solvent and at least one aprotic polar solvent, which most preferably is azeotropic;
(k) optionally drying the sterol crystals obtained to remove the solvent(s); and
(l) optionally melt-drying and particle forming of the sterol crystals.

DEFINITIONS

Before describing in detail exemplary embodiments of the presently claimed invention, definitions important for understanding the presently claimed invention are given.

It is to be understood that this invention is not limited to the particular methodology, protocols, reagents etc. described herein as these may vary, provided that the intention and objective of this invention is or may be achieved with those. It is also to be understood that the terminology used herein is only for the purpose of describing particular embodiments and is not intended to limit the scope of the presently claimed invention that will be limited only by the appended claims. Unless defined otherwise, all technical and scientific terms used herein have the same meanings as commonly understood by one of ordinary skill in the art.

Unless otherwise indicated, the following definitions are set forth to illustrate and define the meaning and scope of the various terms used to describe the invention herein and the appended claims. These definitions should not be interpreted in the literal sense as they are not intended to be general definitions and are relevant only for this application. Meaning of the terms that are not defined herein are generally known to a person skilled in the art or in the literature.

As used in this specification and in the appended claims, the singular forms of "a" and "an" also include the respective plurals unless the context clearly dictates otherwise.

In the context of the presently claimed invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting.

For the purposes of the presently claimed invention the term "consisting of" is considered to be a preferred embodiment of the term "comprising of". If hereinafter a group is defined to comprise at least a certain number of embodiments, this is meant to also encompass a group which preferably consists of these embodiments only.

In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below. Preferably, however, the steps are performed in the order implied by their numerical or hierarchical appellation, i.e. first (a), then (b), then (c) etc. or first i), then ii), then iii) etc.

The term "final sterol product" signifies the phytosterol which is obtained after the purification steps.

The term "(oil) distillate" encompasses edible vegetable oil distillates (VODs), which are even preferred.

The term "(oil) distillation residue" encompasses transesterified oil distillation residues, which are even preferred. Said transesterified oil distillation residues are preferably fatty acid alkyl ester distillation residues, more preferably fatty acid methyl ester distillation residues, in particular from the production of biodiesel.

The term "partial glycerides" encompasses all combinations of mono-, di- and/or triglycerides. In case of oil distillates as starting material, there are only or nearly only triglycerides and nearly no or no mono- and diglycerides, whereas, in case of typical oil distillation residues, there are mainly triglycerides and diglycerides and only a few monoglycerides.

It is also intended that of course the various embodiments and preferred options of the various process steps disclosed herein are to be combined within the actual complete process, so that for a specific performance of this overall process for one process step the general outline is selected, for another process step within this overall process the preferred embodiment and for the again another process step the most preferred option etc. Thus, a general embodiment for one process step can be combined with a preferred embodiment for the next process step and the most preferred embodiment for another process step. All such combinations are in general possible and are encompassed within this present disclosure.

DETAILED DESCRIPTION OF THE INVENTION

Although the presently claimed invention will be described with respect to particular embodiments, this description is not to be construed in a limiting sense.

In a first embodiment, the presently claimed invention relates to a process for the production and purification of sterols from oil distillates, i.e. in step a) of the process an oil distillate is provided.

In a second, preferred embodiment, the presently claimed invention relates to a process for the production and purification of sterols from oil distillation residues, i.e. in step a) of the process an oil distillation residue, in particular a residue of the distillation of transesterified oils is provided.

I. Process for the Production of Sterols a) Raw Materials for Production of Sterols, in Particular Residues from the Distillation of Transesterified Oils:

In an embodiment of the presently claimed invention, residues from the distillation of transesterified, more particularly non-refined oils preferably with a residual acid value below 2, are used as raw materials for the production of sterols.

Such residues may be obtained as outlined herein above, using the known prior art processes. Especially suitable residues are such from the work-up of vegetable oils containing sterols and usually also tocopherols. These residues are obtained by several esterification and transesterifications, treatment with acid etc., all of which is known in the art. One such known process is the process to produce bio-diesel, i.e. methyl fatty acid ester.

Preferably, the oil distillation residue comprises a residue derived from an oil selected from the group consisting of soybean oil, sunflower oil, rapeseed oil, high erucic acid rapeseed oil (HEAR), low eruric acid rapeseed oil (CANOLA; CANadian Oil Low eruic Acid), coconut oil, palm oil, palm kernel oil, and mixtures thereof, more preferably, the oil distillation residue comprises a residue derived from soybean oil, sunflower oil, rapeseed oil such as HEAR or CANOLA, even more preferably, the oil distillation residue comprises a residue derived from sunflower oil, rapeseed oil, preferably HEAR.

These residues are preferably residues from coconut oil, from palm kernel oil, from palm oil, from soybean oil, from sunflower oil, from rapeseed oil such as from HEAR and/or CANOLA, more preferably from soybean oil, sunflower oil, rapeseed oil such as HEAR, even more preferably from sunflower oil and/or rapeseed oil, and especially HEAR, with acid values of 0 to 10, preferably from 0 to 6 and contain mixtures of di- and triglycerides, FMEs, sterol esters, wax esters and free sterols, preferably 1 to 7% by weight triglycerides, 3 to 15% by weight diglycerides, 15 to 40% by weight FMEs, 40 to 50% by weight, in particular 42 to 47% by weight sterol esters, 3 to 4% by weight wax esters and 3 to 15% by weight free sterols and small quantities of monoglycerides.

In another embodiment of the presently claimed invention, oil distillates are used as raw materials for the production of sterols. These distillates are preferably such of coconut oil, of palm kernel oil, of palm oil, of soybean oil, of sunflower oil, of rapeseed oil such as from HEAR and/or CANOLA, more preferably of soybean oil, sunflower oil, rapeseed oil such as from HEAR, even more preferably of sunflower oil and/or rapeseed oil from HEAR, containing 45 to 65% by weight triglycerides and 35 to 55% by weight sterol esters summing up to 100%.

b) First Transesterification Step—Transesterification of the Partial Glycerides (Optional):

If the content of unsaponified matter in the distillate or, preferably, the distillation residue is too low, by this process step combined with process step c), the distillate or distillation residue can be concentrated to a content of unsaponified matter containing sterol esters and usually also tocopherols of about more than 20 such as 35 to 60, preferably 40 to 55 and more preferably 45 to 50 weight percent of unsaponified matter relative to the total weight of concentrated distillate or distillation residue.

In the presently claimed invention, in the "transesterification of the partial glycerides" process step, preferably only the tri-, di- and monoglycerides are reacted with short-chain alcohols to form fatty acid esters. The sterol esters remain substantially bound. Only a small amount of free sterols is formed. Methanol is preferably used as the alcohol, but other lower C2- to C4-alcohols may be used as well but are not preferred.

Preferably, the lower alcohol is added in a quantity of 5 to 40% by weight and preferably 10 to 20% by weight, based on the transesterified oil distillation residue.

Preferably, the lower alcohol is selected from the group consisting of methanol, ethanol and isopropanol.

In a preferred embodiment, methanol is added in a quantity of 5 to 40% by weight and preferably 10 to 20% by weight, based on the transesterified oil distillation residue.

In an embodiment, the reaction is preferably carried out over a period of 2 to 20 minutes, particularly 5 to 20 minutes and even more particularly 8 to 15 minutes at a temperature of 80 to 145° C. and, more particularly preferred, at a temperature of 80 to 100° C. A pressure of 2 to 10 bar, preferably of 2 to 3 bar is spontaneously established at these temperatures. Under these conditions, which correspond to a low-pressure transesterification, a catalyst has to be added, wherein any basic transesterification catalyst may be used as the catalyst.

Preferably, the basic transesterification catalyst is selected from the group consisting of sodium methylate, sodium hydroxide and potassium hydroxide.

In a preferred embodiment, 30% methanolic sodium methylate solution is the preferred basic catalyst and is used in a quantity of preferably 0.5 to 1.8% by weight and more preferably 1.0 to 1.5% by weight, based on the transesterified oil distillation residue.

In another, less preferred embodiment, in an alternative to the low-pressure transesterification, the transesterification may also be carried out under pressure. In this case, the reaction is preferably carried out at 220 to 260° C. and under a pressure of 20 to 80 bar. In the case of residues accumulating in the distillation of oils transesterified under high pressures, there is not any need to add a catalyst because the catalyst—generally soaps of divalent metals, such as Mn, Zn or Ca—is already present in a large excess.

Such high-pressure transesterification may be sensible, if the transesterified oil distillation residues have acid values above 1 and more particularly above 5.

In the presently claimed invention, suitable reactors are, for example, stirred batch autoclaves and continuous reactors such as, for example, turbulent flow tube reactors.

In case optional step b) is applied, step c) is applied comprising steps c.1), c.2), c.3) and/or c.4).

c.1) Removal of the Excess Alcohol (Optional):

In an embodiment of the presently claimed invention, in the "removal of the excess alcohol" process step, the hot reaction mixture from the "transesterification of the partial glycerides" is expanded into a receiver, while 55 to 85% of the excess alcohol is distilling off. The system cools down considerably to 65 to 85° C., preferably to 75 to 85° C., when methanol is used. The residual alcohol which is still left in the reaction product is preferably not distilled off and serves as a solubilizer in the following step.

c.2) Removal of the Catalyst (Optional):

In an embodiment of the presently claimed invention, the catalysts are present in the residues from the distillation of oils transesterified under pressure. These catalysts are preferably Zn soaps (2,000-3,500 ppm), although other soaps are also suitable. The distillation residues may also contain many other metals, such as Fe, Al or Na, in concentrations of up to 300 ppm, and heavy metals, such as Pb, Cr or Ni, in concentrations of up to 20 ppm. Non-metals, such as P, Si or S, are present in concentrations of up to 300 ppm. The catalyst soaps and the other metal compounds are soluble in the reaction mixture from the "transesterification of the partial glycerides".

In order to be able to remove the catalyst, they are preferably converted with acids into insoluble compounds and precipitated as described in EP 0 656 894 B1. Aqueous solutions of citric acid or phosphoric acid are preferably used as the acids. The quantity of acid used is preferably once to twice the molar concentration of metal. At the same time, the addition of acid neutralizes the basic transesterification catalyst, e.g. sodium methylate, used in the low-pressure transesterification of the partial glycerides.

After precipitation, the metal-containing sludge which precipitated is removed. It is preferably centrifuged. Phase separation improves, if 15 to 30% of the excess alcohol remains in the product in the "removal of the excess alcohol" process step.

Alternatively, to centrifugation, the precipitated metals are adsorbed. Preferred absorbers are amorphous silica gels charged with organic acids such as, for example, Trisyl types (specifically, TRISYL® Silica, TRISYL® 4030 Silica, TRISYL® CP2-7887 Silica from the company Grace). Where the metals are removed by adsorption, all the alcohol may be removed in the preceding "removal of the excess alcohol" process step.

In both alternative processes, residual metal contents of less than 1 ppm can be achieved.

c.3) Removal of Glycerol (Optional):

In an embodiment of the presently claimed invention, the catalyst-free product still contains excess alcohol and free glycerol. To prevent any back-reaction in the next "removal of the fatty acid alkyl esters" step, the free glycerol and the residual alcohol are removed from the catalyst-free product by decantation or other means of phase separation, and, if necessary, are washed out with water. The product is then preferably dried.

c.4) Removal of the Fatty Acid Alkyl Esters (Optional):

In order to concentrate the sterol esters, the fatty acid esters are preferably distilled off, for example in a thin-layer evaporator. Methyl esters are preferably distilled at temperatures of 170 to 200° C. and under pressures of 1 to 5 mbar.

According to the presently claimed invention, the partial glycerides were transesterified in the "transesterification of the partial glycerides" process step. Since the sterols are still largely present as sterol esters, they are higher boiling and are not being distilled off during distillation of the fatty acid esters. They remain entirely as a concentrated valuable product in the bottom fraction. In addition, other low-boiling components—if present—may be removed, and preferably are removed at the same time or—even more preferably—sequentially by such distillative process.

In an embodiment of the presently claimed invention, wax esters are also distilled off with the fatty acid esters and are subsequently separated from the fatty acid esters by winterizing. Sterol-free methyl or ethyl esters with a purity of more than 97% are obtained in this way.

A particularly preferred embodiment referring to the process steps b), c1), c3) and c4) is set forth in the following:

The distillate or, preferably, the distillation residue is submitted to a transesterification reaction using a lower alcohol, preferably methanol, as solvent and reactant and a basic transesterification catalyst, preferably sodium methylate, as catalyst. The aim is to convert remaining glycerides in the residue to fatty acid alkyl esters, preferably methyl esters. Following that transesterification, the formed glycerol is to be removed by standard means, e.g. decanting. This process of transesterification with following glycerol removal can be repeated once or twice or more, but one repetition usually is enough and thus a preferred embodiment.

Excess lower alcohol, preferably methanol, is then to be removed, followed by optional further removal of remaining glycerol which can form again as separate phase during or after the removal of lower alcohol, preferably methanol. Then, the formed fatty acid alkyl ester, preferably methyl ester, can be removed, by e.g. distillation, thereby increasing the yield of the fatty acid alkyl ester, i.e. "bio-diesel" in case of the fatty acid methyl ester.

d) Purification Step by Adsorption (Optional):

As a further optional process step, the distillate or, preferably, the distillation residue—or if steps (b) and (c) are applied—the product resulting from step (c), can be subjected to the purification using adsorbents such as clays, earths and oxides. Suitable adsorbents are well-known, e.g. the Trisyl-grades (e.g. (specifically, TRISYL® Silica, TRISYL® 4030 Silica, TRISYL® CP2-7887 Silica from the company Grace). This treatment allows for an improvement of the color, lowering the content of soaps, and/or absorbing trace metals and/or metal ions, preferably all of those improvements, by choosing suitable adsorbents.

This treatment may be performed at ambient or elevated temperature. In view of the high viscosity of the residue or concentrated residue, treatment at elevated temperature is preferable. Suitable temperatures are ambient to about 100° C., with temperatures of around 60 to 90° C. being preferred mainly to a good combination of viscosity and energy cost needed. Suitable treatment duration may be anything from 10 minutes to several hours, e.g. even 5 to 10 hours. Duration mainly depends on the degree of removal desired and the amount of contaminants present in the residue or concentrated residue. Preferably durations are about 0.5 to 10 hours, more preferably 1 to 5 hours, even more preferable 1 to 3 hour, most preferably about 2 hours at 75 to 90° C.

e) Second Transesterification Step—Transesterification of the Sterol Esters:

The sterol esters in the distillate or distillation residue or—if steps (b) and (c) are applied—the product resulting from step (c)—or if step (d) is applied—step (d) are transesterified with a lower alcohol in the presence of a basic catalyst to form free sterols. In case step (b) is omitted, step (e) is of course the first transesterification step. However, for the sake of consistency, it is even then named as "second transesterification step" in the present text.

In an embodiment of the presently claimed invention, the sterol esters are concentrated to more than 20, preferably more than 30, even more preferably more than 40% in the bottom product of the fatty acid ester distillation process. They are converted into free sterols by transesterification with a short-chain C1- to C3-alcohol, preferably methanol, in the presence of a catalyst. Since the transesterification of sterol esters has to take place under more rigorous conditions than the transesterification of partial glycerides, larger quantities of alcohol and catalyst and longer reaction times are necessary.

The quantity of alcohol added is 40 to 80% by weight and preferably 50 to 60% by weight of the bottom product of the fatty acid ester distillation process. Where methanol is the transesterification reagent, 40 to 60% by weight of the bottom product of the fatty acid ester distillation process is used. Here, too, the catalyst may be any basic transesterification catalyst, preferably the ones disclosed above as useable and preferred catalysts as for the first transesterification reaction.

The second transesterification reaction is preferably carried out at a temperature range of 25° C. to 150° C. depending on the pressure and time conditions.

In a first embodiment of the presently claimed invention, the second transesterification reaction takes place over a period of 2 to 10, preferably 4 to 10 hours and more particularly 5 to 8 hours at temperatures of 78 to 145° C. and more particularly 80 to 100° C. and under a pressure of 2 to 10 bar, preferably of 2 to 3 bar. The obvious advantage of this embodiment is the very high conversion to be achieved at relatively short times.

Moreover, by using this embodiment in combination with the first embodiment described for the "first transesterification" step, it has been found that a process for the production of sterols can be made more economical and more friendly to the environment by combining two separate transesterification steps. In a first transesterification step, the mono-, di- and triglycerides are reacted with a lower alcohol in the presence of a basic catalyst. Under the mild conditions, the sterol esters remain predominantly bound and only a small amount of free sterols is formed (<1% by weight). After removal of the excess alcohol, transesterification catalyst and glycerol, the fatty acid esters are removed, preferably distilled, resulting in a concentration of the sterol esters at the bottom of the column.

The sterol esters are then split into the free sterols in a second transesterification step carried out under more extreme conditions. Due to the fact that the impurities are removed in this transesterification step and the sterol esters are present in concentrated form, the free sterols can be obtained under far more economically favorable conditions. The first transesterification step proceeds very quickly and saves time so that it can be carried out in a simple reactor such as—preferably—a tube reactor.

Due to the reduced amounts of starting products, a relatively small stirred reactor is sufficient for the second transesterification.

In a second embodiment of the presently claimed invention, the second transesterification step is carried out at a temperature in the range from room temperature (e.g. 25° C.) to 100° C., preferably to 95° C., more preferably to 90° C. and even more preferably to 88° C., preferably in the range from 40° C. to 75° C. and particularly preferably in the range from 55° C. to 70° C., such as at a temperature of 60 to 65° C., and furthermore in particular at normal pressure and for a period of 5 to 8 hours. The reaction may be performed depending on the temperature and pressure chosen under reflux or without reflux. When methanol is chosen—which is the most favorable alcohol to be employed—the reaction is performed at the boiling temperature of methanol or slightly below when operating at ambient pressure. By this a good temperature control can be implemented.

This embodiment of the invention enables an energy-saving and cost-efficient performance of the method and expensive pressurized reactors and complex and expensive generation and maintenance of the temperatures and pressures are avoided. However, performing the reaction at higher pressures, and thus also higher temperatures, leading to shorter reaction times is of course possible as well (see above), but for energy consumption reasons not preferred.

Furthermore, the low reaction temperature during the second transesterification step contributes to a reduction in the operating costs relative to known methods and, thus, also improves the economy of the method relative to previously customary methods.

However, of course, depending on the duration employed for the transesterifications, at lower temperatures the duration of the reaction has to be prolonged compared to high temperatures, as otherwise no satisfying yields are obtainable. Hence, the net benefit in terms of energy saving depends on the complete outline of the process, the equipment employed and the temperature and duration of the reactions, as a simple reduction in time leads to higher reaction temperature (if the yield should stay the same) or lower yields (if the duration stays the same). Such optimization of parameters in view of the reactor outline based on the guidance disclosed herein is well within the skill of a typical chemical engineer.

II. Crystallization of the Sterols

According to the presently claimed invention, the free sterols produced by the above disclosed process are then purified by crystallization. However, the transesterified oil distillation residues which are preferably used as raw materials in the process according to the presently claimed invention contain impurities which are further concentrated in the product in the process described here and interfere with the crystallization process.

f) Removal of Excess Lower Alcohol, the Basic Catalyst, the Glycerol and/or the Fatty Acid Alkyl Esters (Optional):

According to the presently claimed invention, other process steps, such as flashing of the excess alcohol, catalyst removal and glycerol removal, may optionally be carried out.

Thus, optionally, the excess lower alcohol, the basic catalyst, the glycerol and/or the fatty acid alkyl esters is at least partially removed from the reaction mixture obtained in the "second transesterification" step, preferably at least the lower alcohol and the fatty acid alkyl esters, more preferably at least the lower alcohol, glycerol and the fatty acid alkyl esters, and most preferably all four, each of the components either in one single step or as two, three or more steps with the individual or joint removal of the components being performed in parallel or sequentially. For this, reference is made for the preferred embodiments and features described above for process steps c.1) to c.4).

According to one embodiment (hereinafter referred to as "catalyst removal (II)"), the catalyst used in the transesterification of the sterol esters is soluble in the reaction mixture. In order to be able to remove the catalyst, it is converted with acids into an insoluble compound and precipitated as described in EP 0 656 894 B1. After precipitation, the salt which precipitated is removed. In order to achieve the separation of the organic from the aqueous phase, 30 to 200% by weight and preferably 50 to 100% by weight of FME, based on the amount of product used in the transesterification of the sterol esters, is added to the mixture in accordance with the invention.

g) Adding Water to the Reaction Mixture (Optional):

Optionally, water is added to the reaction mixture obtained in the "second transesterification" step from which, if applicable, the excess lower alcohol, the basic catalyst, the glycerol and/or the fatty acid alkyl esters has at least partially been removed (see above), the water being added in an amount ranging from 15% to 25% based on the mass of a total batch in order to set a mass ratio of sterol:fatty acid alkyl ester (calculated as FME):lower alcohol (calculated as methanol):water of substantially 1:2.5-3:2.2-2.5:0.8-1.2, during the addition of water homogenizing the reaction mixture to form an emulsion/suspension by mixing.

The addition of water makes it possible in a particularly simple manner for substances which would impede crystallization of the sterols to be removed. Thus, by the addition of water, glycerin present in the reaction mixture, catalyst and contaminants are separated off from the reaction mixture, wherein the said substances pass into the water phase. Furthermore, the added water largely extracts the methanol which may still be present in the reaction mixture, so that the solubility of the sterols decreases considerably, and they crystallize out or at least start to crystallize.

Furthermore, during the addition of water to the reaction mixture, it was surprisingly ascertained that when a specific water concentration is reached, a spontaneous, very complete crystallization out of the sterols can already be observed at the reaction temperature, wherein a 3-phase system, consisting of a FME phase, i.e. an organic phase, a water phase and sterol crystals forms simultaneously, wherein the respective density of the three phases increases in the aforesaid sequence.

Thus it has been shown that in particular the addition in the aforesaid quantitative ratio of sterol:fatty acid alkyl ester (calculated as FME):lower alcohol (calculated as methanol): water of substantially 1:2.5-3:2.2-2.5:0.8-1.2 is particularly effective in order to achieve a clear separation of the three phases, whereby further processing of the reaction mixture is greatly simplified, which in turn has an extremely positive effect on the economy of the procedure, in particular with regard to an energy-saving and time-saving reaction of the starting products and obtaining the desired phytosterols.

In order to achieve the separation of the organic from the aqueous phase, 30 to 200% by weight and preferably 50 to 100% by weight of FME, based on the amount of product used in the transesterification of the sterol esters, can be added to the mixture in accordance with the invention.

Optionally, the excess lower alcohol, the basic catalyst, the glycerol and/or the fatty acid alkyl esters is at least partially removed from the 3-phase system, each of the components either in one single step or as two, three or more steps with the individual or joint removal of the components being performed in parallel or sequentially. For this, reference is made for the preferred embodiments and features described above for process steps c.1) to c.4).

h) Crystallization of the Sterols:

According to the presently claimed invention, the free sterols are then purified by crystallization. Successful crystallization typically requires a free sterol concentration of at least 20 to 25% by weight. Sterol concentrations of >40% by weight can be achieved by the process according to the presently claimed invention as described above and thus are highly suitable for this crystallization process step of the present invention as disclosed in the following.

Should the concentration still be below a value which does not allow reasonable crystallization, it can be increased by distilling off the fatty acid esters produced in the "transesterification of the sterol esters" process step. The procedure corresponds to the "removal of the fatty acid alkyl esters" step (see above).

If, according to an embodiment of the presently claimed invention, the transesterification of the sterol esters was carried out under pressure and the metal soaps precipitated were removed by adsorption, FME is advantageously added as solvent. In this case, the quantity of FME is again 30 to 200% by weight and preferably 50 to 100% by weight, based on the amount of product used in the transesterification of the sterol esters.

In an embodiment, the presently claimed invention relates to the purification of sterol fractions which, apart from the lower alcohol, mainly contain fatty acid alkyl, in particular methyl esters, which takes place in a known manner, i.e. the hot mixtures (ca. 50-70° C.) are slowly cooled to form the phytosterol crystals, which are formed at a temperature of from 15° C. to 50° C., preferably 20° C. to 45° C., more preferably 25° C. to 35° C. even more preferably 20° C. to 30° C., in a crystallizer. If necessary, alkaline catalyst from the transesterification present in the mixture can be neutralized beforehand, for example by addition of citric acid or other suitable organic or inorganic acids that are also suitable or acceptable for the intended use of the sterols later on; preferably, such neutralization is omitted if the feed for the crystallization allows for.

In another embodiment, the emulsion/suspension of step (e), (f) or (g) is cooled, in particular in an Armstrong crystallizer (available from the company Armstrong), to a temperature in the range from 15° C. to 50° C., preferably 20° C. to 45° C., more preferably 25° C. to 35° C., to crystallize the sterols as in step (h), wherein the first crystals appear around 65° C. to 50° C., and, when performed not as one batch but as two batches wherein the second batch is the filtered mother liquor of the first batch, the crystals of the first batch appear at around 65° C. and those in the second, consecutive batch at around 55 to 50° C. followed by further slowly cooling to 25° C. to 35° C. to pursue the crystallization.

The lower alcohol is preferably selected from the group consisting of methanol, ethanol and isopropanol. More preferably the lower alcohol is methanol.

In an embodiment of the presently claimed invention, only those mixtures which already have a ratio by weight of sterol to methanol of 100:25 to 100:75 from their production should be used. Otherwise methanol has to be added or distilled off. Under these conditions, the crystallization begins at temperatures of 60-65° C.

In another embodiment of the presently claimed invention, the ratio of sterol:methanol is in the range of 1:0.1 to 1:5, preferably 1:0.5 to 1:3, more preferably 1:0.5 to 1:2.5.

In an embodiment of the presently claimed invention, the phytosterol crystals are formed at a temperature of from 15° C. to 50° C., preferably 20° C. to 45° C., more preferably 25° C. to 35° C., even more preferably 20° C. to 30° C., such as 20° C., 21° C., 22° C., 23° C., 24° C., 25° C., 26° C., 27° C., 28° C., 29° C., 30° C., 31° C., 32° C., 33° C., 34° C. or 35° C.

In another embodiment of the presently claimed invention, the phytosterol crystals are formed at a temperature of from 15° C. to 50° C., and more preferably at every temperature in between 15 and 50° C.

In an embodiment of the presently claimed invention, in order to increase the sterol yield, part of the mother liquor is recycled, for example to the crystallization process, after filtration of the crystal suspension according to process step i). The return stream can be fed to the system together with the fatty acid esters in the "catalyst removal (II)" process step. Alternatively, of course a second, separate crystallization could be performed on the spent mother liquor to obtain even more sterols from it. If desired, a further crystallization or a further recycling to the previous crystallization can occur. Another way of recycling the mother liquor is to introduce it into the first (b) or second (e) transesterification step.

The recycle ratio of the mother liquor depends to a very large extent on the starting material and hence on the composition of the mother liquor. It may be in the range from 0.1 to 5.0 but could in principle be higher as well. A recycle ratio of 0.2 to 3.0 is preferably established.

III. Purification of the Phytosterol i) Removal of the Sterol Crystals by Physical Means from the Mother Liquor:

According to the presently claimed invention, the sterol crystals are separated by physical, in particular mechanical means such as filtration, centrifugation and/or decantation, preferably filtration and/or centrifugation, more preferably filtration.

j) Washing of the Sterol Crystals:

According to the presently claimed invention, the separated sterol crystals are subjected to further purification steps.

According to the presently claimed invention, the sterol crystals are further purified using a solvent or solvent system. The sterol crystals obtained in step i),—either in a separate process step or a combined process step—are purified using an organic solvent and/or a solvent mixture of more than one organic solvents optionally but not preferred also containing water, preferably a solvent mixture that comprises at least one aprotic polar solvent, more preferably a solvent mixture of at least one protic polar solvent and an at least one aprotic polar solvent, which most preferably is an azeotropic mixture.

In an embodiment of the presently claimed invention, the sterol containing phase, which primarily contains sterol crystals, is washed with methanol to wash the crystals free from fatty acid alkyl ester, in particular fatty acid methyl ester, wherein the quantity of methanol is in the range from 20% to 800%, preferably 50 to 800%, more preferably in the range from 125% to 700%, more preferably 125% to 600%, more preferably in the range from 200% to 550%, and especially preferably 200 to 400%, in each case based on the mass of the sterol crystal phase.

In another embodiment of the presently claimed invention, the purification of the sterol crystals preferably occurs in the presence of a solvent system, i.e. a solvent mixture, which comprises at least one polar aprotic solvent.

Preferably, the purification of the sterol fraction occurs in the presence of at least one polar aprotic or non-polar solvent which is selected from the group consisting of ethyl acetate, methyl ethyl ketone and methyl acetate, dichloromethane, N-methyl pyrrolidone, tetrahydrofuran, acetone, dimethylformamide, acetonitrile, dimethyl sulfoxide, heptane, and hexane, with ethyl acetate, acetone, methyl ethyl ketone, methyl acetate, heptane and hexane being preferred.

More preferably, the purification of the sterol fraction occurs in the presence of at least one polar aprotic solvent which is selected from the group consisting of ethyl acetate, methyl ethyl ketone and methyl acetate, dichloromethane, N-methyl pyrrolidone, tetrahydrofuran, acetone, dimethylformamide, acetonitrile, and dimethyl sulfoxide, with ethyl acetate, acetone, methyl ethyl ketone and methyl acetate being preferred, and with ethyl acetate, methyl ethyl ketone and methyl acetate being even more preferred.

Particularly preferably, methyl acetate is used as the sole polar aprotic solvent.

In a preferred embodiment of the presently claimed invention, the purification of the sterol fraction occurs in the presence of at least one polar aprotic solvent and at least one polar protic solvent which are mixed together and/or form an azeotrope in the solvent system, wherein, preferably, the polar protic solvent is selected from the group of water, ethanol, methanol, isopropyl alcohol, butanol and acetic acid, more preferably from the group of water, ethanol, methanol and isopropyl alcohol.

Particularly preferably methanol is used as the sole polar protic solvent.

Preferably, the polar aprotic solvent is present in the range of 25 to 75% by weight, based on the amount of phytosterol, more preferably in the range of 30% to 50% by weight, based on the amount of phytosterol, and every value in between 30% to 50%, based on the amount of phytosterol, with ethyl acetate, methyl ethyl ketone and methyl acetate being the preferred polar aprotic solvent (s), and methyl acetate being more preferred as the sole polar aprotic solvent.

Preferably, the polar protic solvent is present in the range of 5 to 50% by weight, based on the amount of phytosterol, preferably in the range of 10 to 30% by weight, based on the amount of phytosterol, and every value in between 10% to 30%, based on the amount of phytosterol, with methanol being the preferred polar protic solvent.

The sterol crystals could be washed with methyl ester, such as FMEs or methyl acetate, preferably methyl acetate, after washing with at least one polar aprotic solvent and at least one polar protic solvent.

According to an especially preferred embodiment, the sterol containing phase, which primarily contains sterol crystals, is washed 1) optionally at least once with methanol, 2) at least once, preferably one to three times, more preferably two or three times with a solvent mixture of at least one protic polar solvent and at least one aprotic polar solvent, which preferably is an azeotropic mixture, and 3) preferably at least once, more preferably one to three times, even more preferably one or two times with methanol.

Advantageous features and embodiments within this embodiment correspond to the preferred features and embodiments as described herein above for step k).

In a further embodiment of the presently claimed invention, the sterol crystals could be washed with methyl ester, such as methyl and/or ethyl ester, in particular methyl fatty acid ester, after step i) and before step j) to "pre-wash" the crystals further to further increase the purity and/or color of the to be obtained sterol crystals.

k) Further Drying the Sterols (Optional):

The washed sterol crystals can be dried using conventional dryers of all kinds, to remove remaining solvents. Application of reduced pressure helps to increase the removal of solvent traces. This step serves a drying or "pre-drying", depending on the method employed and the desired content of residual solvent in the final sterol product to be obtained. The latter of course mainly depends on the intended use of the sterols.

Thus, in an embodiment the sterols obtained as sterol crystals may be further dried by e.g. stream stripping at a temperature of 150° C. to 170° C. for 1 to 3 hours to remove the solvent.

l) Further Purifying the Sterols by Melt-Drying to Remove Trace Amounts of Solvents within the Sterols (Optional):

Following the "conventional" drying of the previous step k), the (pre-)dried crystals can be melted preferably under reduced pressure to remove solvent traces enclosed within the crystals. By this, the residual content of solvents can be lowered even more so as to achieve certain higher product qualities being usable also for critical applications, e.g. direct applications to human beings in nutritional or pharmaceutical products.

The melted sterols need to be solidified. That could be done either by simple cooling with stirring of any kind, e.g. in an extruder, a paddle dryer and the like. Other known methods for solidification of melts are prilling, in apparatuses such as prillers including jet-prillers, which can form droplets close to spherical shapes, or simply in dripping towers, in which molten material is dropped into colder air or gases, all such methods to finally obtain solid, particulate sterols, which are preferably in forms that do not show dusting but good flowability and preferably a high density, to obtain sterols particulates with easy handling properties. Also, clandering, pressing, melting and spray-(dry)-ing are suitable particle forming processes.

Thus, in a further embodiment, the sterols obtained—and preferably (pre-)dried—are subjected to a particle forming process, preferably to prilling, more preferably to jet-prilling, which is preferably done under liquid nitrogen, to obtain solid, close to spherical, low to non-dusting sterol particles of very low organic solvent-content, which are suitable for direct use including oral intake by humans.

In an embodiment of the presently claimed invention, for measurement of the Gardner color number, the phytosterol is provided in the form of a 10% by weight solution in pyridine. Preferably, the final sterol product has a Gardner color number of less than 4.0, when measured for a 10 wt. % of sterol in pyridine. More preferably, the final sterol product has a Gardner color number of less than 3.0, preferably less than 2.0, more preferably less than 1.5, even more preferably less than 1, such as less than 0.9, 0.8, 0.7, 0.6, 0.5 and any value in between and below 4 and 0.5, when measured for a 10 wt. % of the sterol in pyridine.

Preferably, the solvent content in the purified phytosterol is less than 100 ppm, more preferably less than 50 ppm, more preferably less than 20 ppm, and even more preferably less than 10 ppm such as 5 or 1 ppm or even below, and every value in between 100 and 1 ppm, based on the total weight of the purified phytosterol.

Preferably, the sterol ester content in the purified phytosterol is less than 10% by weight, more preferably less than 5% by weight, more preferably less than 2% by weight, even more preferably less than 1% by weight, and most preferably less than 0.5% by weight, such as 0.1, 0.05% by weight and every value in between 5 and 0.05% by weight and below, based on the total weight of the purified phytosterol.

Advantages:

The presently claimed invention is associated with at least one of the following advantages:
1. The process is suitable for various starting mixtures and does not involve the use of toxicologically and ecologically unsafe solvents.
2. The better utilization of the distillation residues leads to an economic, ecologically safe process that is easy to carry out on an industrial scale.
3. Lower energy consumption due to lower pressure/temperature for the transesterification(s)
4. The phytosterols are obtained with a Gardner color number of less than 4.
5. The phytosterols are obtained in a high yield with a very low content of sterol ester (i.e. <10%) by using the above described purification process.
6. The solvent content of the final product is low (less than 100 ppm)

Last not least, the present invention relates to the following two especially preferred embodiments:

1. A process for producing sterols, said process comprising:
   (a) providing an oil distillation residue, said residue comprising sterol esters and partial glycerides;
   (b) transesterifying the partial glycerides with a lower alcohol in the presence of a basic catalyst to form fatty acid alkyl esters and glycerol;
   (c) removing excess lower alcohol, the basic catalyst, the glycerol and the fatty acid alkyl esters, each of the four components either in one single step or as two, three or more steps with the removal of the four components being performed in parallel or sequentially, to form a product comprising the sterol esters; and
   (d) see step (d) before;
   (e) transesterifying the sterol esters at a temperature of from 25° C. to 90° C. and at atmospheric pressure to form free sterols with a lower alcohol in the presence of a basic catalyst;
   (f) see step (f) before;
   (g) optionally adding water to a reaction mixture of step (e) or—if step (f) is applied—step (f) the water being added in an amount ranging from 15% to 25% based on the mass of a total batch in order to set a mass ratio of sterol:fatty acid alkyl ester (calculated as FME):lower alcohol (calculated as methanol):water of substantially 1:2.5-3:2.2-2.5:0.8-1.2, during the addition of water homogenizing the reaction mixture to form an emulsion/suspension by mixing,
   (h) crystallize sterols in the mixture obtained from step (e), (f) or (g); optionally under mixing,
   (i) removal of the sterols by physical means from the mother liquor,
   (j) washing the sterol crystals obtained in step (i), in a separate or combined washing with at least one solvent, wherein the solvent is an azeotrope of a protic polar solvent and aprotic polar solvent, wherein the protic polar solvent is selected from the group consisting of water, ethanol, methanol, isopropyl alcohol and the aprotic polar solvent is selected from the group consisting of ethyl acetate, methyl ethyl ketone and methyl acetate,
   (k) optionally drying the sterol crystals obtained to remove the solvent,
   (l) optionally melt-drying and particle forming of the sterol crystals by thermal forming such as prilling, e.g. jet prilling, clandering, pressing, melting and spray-(dry)-ing,
   (m) wherein optionally repeating the steps (h) to (j) by re-dissolving the sterol in a lower alcohol between steps (j) and (k).

2. A process for producing sterols, said process comprising:
   (a) providing an oil distillation residue, said residue comprising sterol esters and partial glycerides;

(b) transesterifying the partial glycerides with a lower alcohol in the presence of a basic catalyst to form fatty acid alkyl esters and glycerol;
(c) removing excess lower alcohol, the basic catalyst, the glycerol and the fatty acid alkyl esters, each of the four components either in one single step or as two, three or more steps with the removal of the four components being performed in parallel or sequentially, to form a product comprising the sterol esters; and
(d) see step (d) before;
(e) transesterifying the sterol esters at a temperatures of 90 to 145° C., more particularly 120 to 130° C. for 4 to 10 hours and more particularly 5 to 8 hours at and under a pressure of 2 to 10 bar with a lower alcohol in the presence of a basic catalyst;
(f) see step (f) before;
(g) optionally adding water to a reaction mixture of step (e) or—if step (f) is applied—step (f) the water being added in an amount ranging from 15% to 25% based on the mass of a total batch in order to set a mass ratio of sterol:fatty acid alkyl ester (calculated as FME):lower alcohol (calculated as methanol):water of substantially 1:2.5-3:2.2-2.5:0.8-1.2, during the addition of water homogenizing the reaction mixture to form an emulsion/suspension by mixing,
(h) crystallize sterols in the mixture obtained from step (e), (f) or (g); optionally under mixing,
(i) removal of the sterols by physical means from the mother liquor,
(j) washing the sterol crystals obtained in step (i), in a separate or combined washing with at least one solvent, wherein the solvent is an azeotrope of a protic polar solvent and aprotic polar solvent, wherein the protic polar solvent is selected from the group consisting of water, ethanol, methanol, isopropyl alcohol and the aprotic polar solvent is selected from the group consisting of ethyl acetate, methyl ethyl ketone and methyl acetate,
(k) optionally drying the sterol crystals obtained to remove the solvent,
(l) optionally melt-drying and particle forming of the sterol crystals by thermal forming such as prilling, e.g. jet prilling, clandering, pressing, melting and spray-(dry)-ing
(m) wherein optionally repeating the steps (h) to (j) by re-dissolving the sterol in a lower alcohol between steps (j) and (k).

EXAMPLES

The presently claimed invention will now be illustrated in more detail by reference to the following specific, non-limiting examples.

Example 1

2.5 kg of residue from the distillation of transesterified palm kernel oil with a residual acid value of 3.5 was transesterified with 375 g (=15%) of methanol in the presence of 37.5 g (=1.5%) of sodium methylate at 122° C. A pressure of 5 bar built up. After 8 minutes, the reaction mixture was drained off into a glass flask into which 58 g (=2.3%) of 50% citric acid solution was introduced. 80% of the excess methanol was "flashed off" and at the same time the catalyst was neutralized. The mixture cooled down to 75° C.

After stirring for 15 minutes, 250 g of water was added, and stirring was continued for another 60 minutes at 75° C. The mixture was then cooled, and the aqueous phase was drained off. The organic phase was washed twice with 250 g of water.

To remove the FME, the product was distilled in a thin-layer evaporator at 180° C. and 3 mbar. The feed was run in at 90° C. The temperature of the condenser was 50° C. A ratio of distillate to bottom product of 75:25 was obtained for a throughput of 150 g/min. The methyl ester yield was thus 70%, based on the residue from the distillation of transesterified palm kernel oil.

130 g of the bottom product were then transesterified by addition of 65 g (=50%) of methanol and 2.6 g (=2.0%) of Na methylate at 120° C. After 5 h, the reaction was stopped by addition of 4.0 g (=3.1%) of 50% citric acid and the excess methanol was flashed off. The mixture was cooled to 75° C.

After stirring for 15 min, 13 g of water were added to the reaction mixture and, after stirring for another 30 min at 75° C., 110 g of FME were added to facilitate phase separation. Phase separation took place at 60° C. After separation of the aqueous phase, the organic phase was washed with 39 g of water. Then:

a) The organic phase was heated to 65° C., after which the stirrer and the heating were switched off. After 60 min, the mixture cooled down to 25° C. and the maximum possible amount of crystals was obtained, or b) The organic phase was heated to 65° C. and then poured into an unheated vessel. After 25 min, the mixture cools down to below 30° C. and the maximum possible amount of crystals was obtained.

The crystals obtained in examples 1a) and 1b) were washed with suitable solvents. After drying, sterols were obtained in a yield of 15.5 g, corresponding to 42.7%, based on the total sterol content of the residue from the distillation of transesterified palm kernel oil. The sterol concentration in the final product was >95%.

Example 2

The procedure described in Example 1 was repeated up to and including transesterification of the sterol esters. In the subsequent washing step, 20% of the mother liquor obtained in example 1b) was also added to the mixture in addition to the 110 g of FME. All other steps were carried out as in Example 1, crystallization being carried out as in Example 1b).

By recycling 20% of the mother liquor, the sterol yield was increased to 19 g and, hence, to 52.3%, based on the total sterol content of the residue from the distillation of transesterified palm kernel oil. The sterol concentration in the final product was >95%.

Example 3

As raw, i.e. starting material rapeseed methyl ester distillation residue having a content of unsaponified matter of 20 to 25 percent by weight was chosen.

To convert the remaining glycerides in the residue into methyl esters, a transesterification was conducted by means of methanol as reactant and sodium methylate as catalyst for 10 min at 80° C. under 2.5 bar with subsequent removal of the glycerol thereby produced. Said transesterification and glycerol removal was repeated then before the excess of methanol was removed—so-called de-methanolysation—followed by, once again, the removal of glycerol. Finally, the methyl esters formed during the transesterification were removed by means of distillation.

By the process as set forth before, the unsaponified matter in the residue was concentrated to about 45 to 50 percent by weight.

To purify the concentrated residue, i.e. improve the color, lower the soap content and adsorb traces of metals, a treatment with Trisyl (an activated earth available from the company from the company Grace, specifically, TRISYL® Silica, TRISYL® 4030 Silica, TRISYL® CP2-7887 Silica) was performed for 2 hours at 80° C. followed by removal of Trisyl by means of filtration.

To convert the sterol esters in the concentrated residue into free sterols, another transesterification was conducted by means of methanol as reactant and sodium methylate as catalyst for 6 to 7 hours at 60 to 65° C. under atmospheric pressure.

Crystallization of the sterols was subsequently conducted by slowly cooling the reaction mixture which, based on the content of sterols, additionally contained 100% by weight of methanol in an Armstrong crystallizer (available from the Company Armstrong) down to 25 to 30° C.

On completion of the crystallization, the crystals were filtered off, washed free from FME with pure methanol and dried to constant weight.

Example 4—Purification of the Sterol Crystals

The sterol crystals obtained by a process as described and disclosed in Example 3 were submitted to the following purification steps.

On completion of the crystallization according to Example 3 and under nitrogen (up to 2 bars), the crystals were filtered off, washed free from FME with pure methanol and further subjected to washings with the following solvents:
   ethyl acetate and its azeotrope with methanol, or
   methyl ethyl ketone and its azeotrope with methanol, or
   methyl acetate and its azeotrope with methanol,
   with subsequent pure methanol washing.

Further the crystals were melt-dried to constant weight and subjected to particle forming by prilling.

The results obtained were compared to experiments, in which the crystals were washed with FME with subsequent pure methanol washing.

The results obtained are summarized in Tables 1-3 (laboratory scale) as well as in Tables 1a-3a (commercial scale, e.g. plant level). In each table, example C1 and T1 refer to the same sterol batch originating from the same rapeseed methyl ester distillation residue. The same applies to C2 and T2, C3 and T3 as well as C4 and T4 (if applicable). Thus, example C1 has to be compared with example T1 and so on.

TABLE 1

Solvent used is azeotrope of ethyl acetate with methanol (laboratory scale)

| Expt. No. | Solvent for washing | Color | Purity | Yield |
|---|---|---|---|---|
| C1 | 1 washing of FME + 3 washings of methanol | 2.1 | 98.8 | 73.7 |
| C2 | 1 washing of FME + 3 washings of methanol | 2.4 | 96.8 | 65.6 |
| C3 | 1 washing of FME + 3 washings of methanol | 4 | 98.4 | 58.1 |
| C4 | 1 washing of FME + 3 washings of methanol | 1 | 99.6 | 72 |
| T1 | 2 washings of azeotrope of ethyl acetate/methanol + 1 washing of methanol | 1.2 | 99.5 | 74.6 |
| T2 | 2 washings of azeotrope of ethyl acetate/methanol + 1 washing of methanol | 1.2 | 98.4 | 72.6 |
| T3 | 2 washings of azeotrope of ethyl acetate/methanol + 1 washing of methanol | 3 | 100 | 69.5 |
| T4 | 2 washings of azeotrope of ethyl acetate/methanol + 1 washing of methanol | 0.6 | 99.7 | 72 | n.d. = not determined

TABLE 1a

Solvent used is azeotrope of ethyl acetate with methanol (commercial scale)

| Expt. No. | Solvent for washing | Color | Purity | Yield |
|---|---|---|---|---|
| C1 | 1 washing of FME + 3 washings of methanol | 2.7 | n.d. | 62.5 |
| T1 | 2 washings of azeotrope of ethyl acetate/methanol + 1 washing of methanol | 0.7 | n.d. | 61.2 | n.d. = not determined

TABLE 2

Solvent used is azeotrope of methyl ethyl ketone with methanol (laboratory scale)

| Expt. No. | Solvent for washing | Color | Purity | Yield |
|---|---|---|---|---|
| C1 | 1 washing of FME + 3 washings of methanol | 3.6 | 99.2 | 54.4 |
| C2 | 1 washing of FME + 3 washings of methanol | 2.7 | 99.1 | 62.0 |
| C3 | 1 washing of FME + 3 washings of methanol | 4 | 98.4 | 58.1 |
| T1 | 2 washings of azeotrope of methyl ethyl ketone/methanol + 1 washing of methanol | 1.9 | 99.3 | 70.3 |
| T2 | 2 washings of azeotrope of methyl ethyl ketone/methanol + 1 washing of methanol | 1.9 | 99.4 | 75.7 |
| T3 | 2 washings of azeotrope of methyl ethyl ketone/methanol + 1 washing of methanol | 2.8 | 99.4 | 70.6 | n.d. = not determined

TABLE 2a

Solvent used is azeotrope of methyl ethyl ketone with methanol (commercial scale)

| Expt. No. | Solvent for washing | Color | Purity | Yield |
|---|---|---|---|---|
| C1 | 1 washing of FME + 3 washings of methanol | 1.9 | n.d. | 59.2 |
| T1 | 2 washings of azeotrope of methyl ethyl ketone/methanol + 1 washing of methanol | 1.2 | n.d. | 64.9 | n.d. = not determined

TABLE 3

Solvent used is azeotrope of methyl
acetate with methanol (laboratory scale)

| Expt. No. | Solvent for washing | Color | Purity | Yield |
|---|---|---|---|---|
| C1 | 1 washing of FME + 3 washings of methanol | 4 | 98.4 | 58.4 |
| C2 | 1 washing of FME + 3 washings of methanol | 2.7 | 99.1 | 62.6 |
| C3 | 1 washing of FME + 3 washings of methanol | 3.6 | 99.1 | 62.6 |
| C4 | 1 washing of FME + 3 washings of methanol | 3.0 | 100 | 75.1 |
| T1 | 2 washing of azeotrope of methyl acetate/methanol + 1 washing of methanol | 3.2 | 99.3 | 71.8 |
| T2 | 2 washing of azeotrope of methyl acetate/methanol + 1 washing of methanol | 1.2 | 99.1 | 74.7 |
| T3 | 2 washing of azeotrope of methyl acetate/methanol + 1 washing of methanol | 1.6 | 99.1 | 74.7 |
| T4 | 3 washing of azeotrope of methyl acetate/methanol | 0.5 | 100 | 77 | n.d. = not determined

TABLE 3a

Solvent used is azeotrope of methyl
acetate with methanol (commercial scale)

| Expt. No. | Solvent for washing | Color | Purity | Yield |
|---|---|---|---|---|
| C1 | 1 washing of FME + 3 washings of methanol | 2.2 | n.d. | 62.7 |
| T1 | 2 washings of azeotrope of methyl acetate/methanol + 1 washing of methanol | 1.0 | n.d. | 67.7 | n.d. = not determined

CONCLUSIONS

According to Table 1 (laboratory scale), the color of the final sterol product is remarkedly better in case of T1 to T4 than in case of C1 to C4. In comparison to the latter, the purity is at least slightly better, whereas, the yield is at least the same or even better for T1 to T4. As can be taken from Table 1a (plant level), the color is strongly improved for T1 compared to C1, whereas, the yield more or less stays the same.

According to Table 2 (laboratory scale), the color and especially the yield of the final sterol product is remarkedly better in case of T1 to T3 than in case of C1 to C3. In comparison to the latter, the purity is slightly better for T1 to T3. As can be taken from Table 2a (plant level), color and yield are improved for T1 compared to C1.

According to Table 3 (laboratory scale), the yield and especially the color of the final sterol product is remarkedly better in case of T1 to T4 than in case of C1 to C4. In comparison to the latter, the purity is at least the same or even slightly better for T1 to T4. As can be taken from Table 3a (plant level), color and yield are improved for T1 compared to C1.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the presently claimed invention as defined by the appended claims.

The invention claimed is:

1. A process for producing and purifying sterols, said process comprising at least the steps of:
   (a) providing an oil distillate or an oil distillation residue, said distillate or residue comprising sterol esters and partial glycerides,
   (b) transesterifying the partial glycerides with a lower alcohol in the presence of a basic catalyst to form fatty acid alkyl esters and glycerol,
   (c) removing at least partially the excess lower alcohol, the basic catalyst, the glycerol and/or the fatty acid alkyl esters, each of the components either in one single step or as two, three or more steps with the removal of the components being performed in parallel or sequentially, to form a product comprising the sterol esters,
   (d) subjecting the product resulting from step (c) to a purification step using adsorbents;
   (e) transesterifying the sterol esters in the distillate with a lower alcohol in the presence of a basic catalyst to form free sterols,
   (f) removing at least partially the excess lower alcohol, the basic catalyst, the glycerol and/or the fatty acid alkyl esters, each of the components either in one single step or as two, three or more steps with the individual or joint removal of the components being performed in parallel or sequentially,
   (g) adding water to the product resulting from step (e) or step (f), the water being added in an amount ranging from 15% to 25%, based on the mass of a total batch in order to set a mass ratio of sterol:fatty acid alkyl ester (calculated as FME):lower alcohol (calculated as methanol):water of substantially 1:2.5-3:2.2-2.5:0.8-1.2, during the addition of water homogenizing the reaction mixture to form an emulsion/suspension by mixing,
   (h) crystallize sterols in the mixture obtained from step (e), (f) or (g);
   (i) removing of the sterol crystals by physical means from the mother liquor,
   (j) washing the sterol crystals obtained in step (i), in one or more separate or combined washing(s) with a solvent, wherein the solvent is a solvent mixture, wherein the solvent is an azeotrope, of at least one protic polar solvent and at least one aprotic polar solvent, wherein the protic polar solvent is selected from the group consisting of water, ethanol, methanol and isopropanol, and the aprotic polar solvent is selected from the group consisting of ethyl acetate, methyl ethyl ketone and methyl acetate,
   (k) optionally drying the sterol crystals to remove the solvent, and
   (l) optionally melt-drying and particle forming of the sterol crystals.

2. The process according to claim 1, wherein in step a) an oil distillation residue being vegetable oil-derived is provided.

3. The process according to claim 2, wherein the oil distillation residue comprises a residue derived from an oil selected from the group consisting of soybean oil, sunflower oil, rapeseed oil, high erucic acid rapeseed oil (HEAR), coconut oil, palm oil, palm kernel oil, and mixtures thereof.

4. The process according to claim 3, wherein the oil distillation residue comprises a residue derived from sunflower oil, rapeseed oil or high erucic acid rapeseed oil (HEAR).

5. The process according to claim 1, wherein step (b) is applied and in step (b) the transesterification of the partial glycerides is carried out at a temperature of from 80° C. to 145° C. and a pressure of from 2 to 10 bar for a period of from 5 to 20 minutes.

6. The process according to claim 5, wherein the transesterification of the partial glycerides is carried out at a temperature of from 80° C. to 100° C. and a pressure of from 2 to 3 bar for a period of from 8 to 15 minutes.

7. The process according to claim 1, wherein the lower alcohol comprises alcohol selected from the group consisting of methanol, ethanol and isopropanol.

8. The process according to claim 7, wherein the lower alcohol is methanol.

9. The process according to claim 1, wherein steps (b) and (c) are applied and in step (c) removing excess lower alcohol is applied which comprises allowing expansion until the reaction temperature has cooled to a temperature of from 65° C. to 85° C.

10. The process according to claim 1, wherein the basic catalyst is selected from the group consisting of sodium methylate, sodium hydroxide and potassium hydroxide.

11. The process according to claim 1, wherein steps (b) and (c) are applied and in step (c) the removal of the basic catalyst is applied which comprises the addition of an aqueous solution of an acid, precipitation of the catalyst and separation of the precipitate.

12. The process according to claim 1, wherein steps (b) and (c) are applied and in step (c) the fatty acid alkyl esters are removed by distillation.

13. The process according to claim 12, wherein the distillation is carried out at a temperature of from 170° C. to 200° C. and a pressure of from 1 to 5 mbar.

14. The process according to claim 1, wherein in step (e) the transesterification of the sterol esters is carried out at a temperature of from 40° C. to 70° C. at atmospheric pressure for a period of 5 to 8 hours.

15. The process according to claim 1, wherein in step (e) the transesterification of the sterol esters is carried out for a period of 4 to 10 hours at temperatures of 80 to 145° C. and under a pressure of 2 to 10 bar.

16. The process according to claim 1, wherein the method further comprises cooling the emulsion/suspension of step (e), (f) or (g) to a temperature in the range from 15° C. to 50° C. to crystallize the sterols as in step (h), wherein the first crystals appear around 65° C. to 50° C., and when performed not as one batch but as two batches wherein the second batch is the filtered mother liquor of the first batch, the crystals of the first batch appear at around 65° C. and those in the second, consecutive batch at around 55 to 50° C. followed by further slowly cooling to 25° C. to 35° C. to pursue the crystallization.

17. The process according to claim 1, wherein the sterol crystals in step (i) are separated by physical means including filtration, centrifugation and/or decantation from the mother liquor.

18. The process according to claim 1, wherein in step (j) washing comprises the use of methyl esters.

19. The process according to claim 18, wherein the methyl esters are selected from the group of FMEs and methyl acetate.

20. The process according to claim 1, wherein the drying of sterols in step (k) is done by stream stripping at a temperature of 150° C. to 170° C. for 1 to 3 hours to remove the solvent.

21. The process according to claim 1, wherein the particle forming in step (l) is done by prilling under liquid nitrogen.

* * * * *